(12) United States Patent
Yun et al.

(10) Patent No.: US 11,000,590 B2
(45) Date of Patent: May 11, 2021

(54) VIRUS-PCION COMPLEX HAVING ENHANCED ANTITUMOR EFFECT BY USING ELECTROMAGNETIC FIELD

(71) Applicant: INDUSTRY-UNIVERSITY COOPERATION FOUNDATION HANYANG UNIVERSITY, Seoul (KR)

(72) Inventors: Chae Ok Yun, Seoul (KR); Joung-Woo Choi, Seoul (KR)

(73) Assignee: GENEMEDICINE CO., LTD. (KR)

( * ) Notice: Subject to any disclaimer, the term of this patent is extended or adjusted under 35 U.S.C. 154(b) by 0 days.

(21) Appl. No.: 16/432,825

(22) Filed: Jun. 5, 2019

(65) Prior Publication Data

US 2019/0298831 A1    Oct. 3, 2019

Related U.S. Application Data

(62) Division of application No. 15/458,685, filed on Mar. 14, 2017, now Pat. No. 10,357,564.

(30) Foreign Application Priority Data

Mar. 14, 2016    (KR) .................. 10-2016-0030514

(51) Int. Cl.
| | |
|---|---|
| A61K 41/00 | (2020.01) |
| C12N 7/00 | (2006.01) |
| C12N 15/86 | (2006.01) |
| A61K 9/51 | (2006.01) |
| A61K 47/60 | (2017.01) |
| A61K 47/64 | (2017.01) |
| A61K 47/69 | (2017.01) |
| A61K 35/761 | (2015.01) |

(52) U.S. Cl.
CPC ............ *A61K 41/00* (2013.01); *A61K 9/5146* (2013.01); *A61K 9/5169* (2013.01); *A61K 41/0052* (2013.01); *A61K 47/60* (2017.08); *A61K 47/645* (2017.08); *A61K 47/6923* (2017.08); *A61K 47/6941* (2017.08); *C12N 7/00* (2013.01); *C12N 15/86* (2013.01); *A61K 35/761* (2013.01); *C12N 2710/10332* (2013.01); *C12N 2710/10343* (2013.01)

(58) Field of Classification Search
None
See application file for complete search history.

(56) References Cited

U.S. PATENT DOCUMENTS

2013/0323206 A1* 12/2013 Yun ..................... C12N 15/85
424/93.2

FOREIGN PATENT DOCUMENTS

CN    103114435    5/2013

OTHER PUBLICATIONS

Park, Macromolecular Bioscience, 14, 2014 (Year: 2014).*
Harrington, Nature Reviews Drug Discovery, 18, 2019 (Year: 2019).*
Park, Biomacromolecules, 12, 2011 (Year: 2011).*
Smith, Oncolytic Virotherapy, 2014 (Year: 2014).*
Jung, Biomacromolecules, 16, 2014 (Year: 2014).*
Chorny, Molecular Pharmaceutics, 6, 5, 2009 (Year: 2009).*
Choi et al., "Using a magnetic field to redirect an oncolytic adenovirus complexed with iron oxide augments gene therapy efficacy", Biomaterials 65 (2015) 163-174.
Park, Biomacromolecules, 12, 2011.
Park, Macromolecular Bioscience, 14, 2014.

* cited by examiner

*Primary Examiner* — Susan T Tran
*Assistant Examiner* — William Craigo
(74) *Attorney, Agent, or Firm* — Adsero IP

(57) ABSTRACT

The present disclosure relates to a composition for transduction of a virus in a cell by using a crosslinked product of PEGylated magnetic nanoparticles and catechol grafted poly-L-lysine by application of an external magnetic field. When the composition is used, a virus may be delivered into cells more rapidly and efficiently than in intracellular uptake of a virus by CAR-mediated endocytosis.

7 Claims, 10 Drawing Sheets

1: PBS, 2: HmT, 3: HmT-PCION, 4: HmT-PCION+MGF

VIRUS-PCION COMPLEX HAVING ENHANCED ANTITUMOR EFFECT BY USING ELECTROMAGNETIC FIELD

CROSS-REFERENCE TO RELATED APPLICATION

This application is a divisional of U.S. patent application Ser. No. 15/458,685, filed Mar. 14, 2017, entitled "VIRUS-PCION COMPLEX HAVING ENHANCED ANTITUMOR EFFECT BY USING ELECTROMAGNETIC FIELD", which application claims priority to and the benefit of Korean Patent Application No. 2016-0030514, filed on Mar. 14, 2016, the disclosures of which is incorporated herein by reference in their entirety.

BACKGROUND

1. Field of the Invention

The present invention relates to a composition for transfecting an anti-tumor virus into a tumor cell using a cross-linked product of PEGylated magnetic nanoparticles and catechol-grafted poly-L-lysine when an external magnetic field is applied.

2. Discussion of Related Art

Successful cancer gene therapy requires a delivery system that is nontoxic, and can achieve efficient in vivo transduction and transgene expression. Adenovirus (Ad) serotype-5 has been widely used in clinical applications due to its high titer ability, high transduction efficiency in both dividing and non-dividing cells, and the absence of genomic integration-mediated mutagenesis. Several clinical trials have reported the successful use of locally injected Ads for cancer gene therapy. Ad-based cancer gene therapy has continued to develop with cancer cell-specific replicating oncolytic Ads that are far superior to conventional technologies. Oncolytic Ad has many advantages, including the ability to self-propagate, lyse infected cancer cells, and produce 1,000 to 10,000 copies of progeny per infected cell, thus causing secondary infection of neighboring cancer cells in a tumor. Therapeutic gene-inserted oncolytic Ads show high gene-delivery efficiency and potential antitumor efficacy, in vitro and in vivo. However, Ads are dependent on the coxsackievirus and adenovirus receptor (CAR) for target cell entry, limiting the clinical efficacy of Ad-mediated cancer gene therapy. Earlier studies have demonstrated that cells with low CAR expression show poor Ad infectivity. Thus, overcoming the transduction efficiency of Ads in CAR-negative tumors is a crucial step in improving the therapeutic efficacy of oncolytic Ads.

Currently, hybrid vectors that combine the advantages of both viral and non-viral components are available. One proposed strategy to overcome the limitations of Ads' CAR-dependence is to modify the Ad surface with a polymer that bypasses the need for CAR-mediated endocytosis. Modifying Ads with cationic polymers or lipids enhances Ad-mediated gene delivery. However, these strategies do not address targeted tumor-specific Ad-mediated gene delivery because injected polymer/lipid-modified Ads rapidly disseminate into surrounding non-target tissues.

Magnetic nanoparticles provide accelerated vector accumulation in target sites when directed with magnetic field-enforced delivery. This approach is customizable by adjusting particle size, surface charge density, and surface functionality with therapeutic drugs or genes, and results in enhanced cellular uptake and replication efficacy, and specific delivery to target tissues.

Coupling Ad viruses to polyethyleneimine (PEI)-coated super-paramagnetic iron oxide ($Fe_3O_4$) nanoparticles improves gene transfection efficiency when these vectors are directed by an external magnetic force (MGF). Considering the point that the usage of 25 kDa PEI is limited in vivo due to substantial cytotoxicity, magnetofection with PEI-coated superparamagnetic iron oxide nanoparticle-coated Ad can provide a strong platform for efficient and safe delivery of therapeutic genes. Moreover, the PEI coating on magnetic nanoparticles condenses anionic nucleotides such as plasmid DNA and siRNA into compact complexes, and facilitates their escape from endosomes via the proton sponge effect. Gene delivery mediated by magnetic nanoparticles exhibits higher transfection efficiency compared to conventional polyplex transfection. Park et al. (J. W. Park, K. H. Bae, C. Kim, T. G. Park, Clustered magnetite nanocrystals cross-linked with PEI for efficient siRNA delivery, Biomacromolecules 12 (2011) 457-465.) disclosed that clustered, magnetized, PEI-encapsulated, super-paramagnetic $Fe_3O_4$ particles enhance magnetization properties and sustain super-paramagnetism, without exhibiting magnetic hysteresis. These particles induce faster sedimentation and greater accumulation within cells, and deliver drugs or genes rapidly under an MGF. In addition, PEG-coated, cross-linked, iron oxide nanoparticles (PCIONs) have been known to deliver plasmid DNA into mesenchymal stem cells efficiently in response to an external MGF.

The present disclosure is aimed to improve the therapeutic efficacy of oncolytic Ads in vitro and in vivo in combination with PCIONs.

Many papers and patent documents are referenced and citation thereof is marked throughout the present specification. The disclosures of which are incorporated herein by reference in its entirety to more clearly describe the level of the art to which the present application pertains and the content of the present disclosure.

SUMMARY OF THE INVENTION

The inventors of the present disclosure had made intensive efforts to develop a pharmaceutical composition for anticancer therapy, including an antitumor adenovirus and having enhanced transduction efficiency of an antitumor adenovirus in a tumor cell. As a result, they verified that, when a composition, prepared by combining an antitumor adenovirus with a cross-linked product of PEGylated magnetic nanoparticles and catechol-grafted poly-L-lysine, was used, transduction efficiency thereof in a tumor cell was significantly increased by application of an external magnetic field, thus completing the present application.

Thus, it is one object of the present disclosure to provide a complex including: (a) magnetic nanoparticles crosslinked with catechol grafted poly-L-lysine and having PEGylated surfaces; and (b) a virus.

It is another object of the present disclosure to provide a method of enhancing transduction efficiency of a virus in a cell, the method including:

administering the above-described complex to an individual; and applying an external magnetic field to the complex-administered individual.

It is still another object of the present disclosure to provide a method of treating cancer, the method including administering the above-described complex to an individual.

The other technical goals and advantages of the present disclosure are more clearly understood by the detailed description, claims, and the accompanying drawings.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1A:
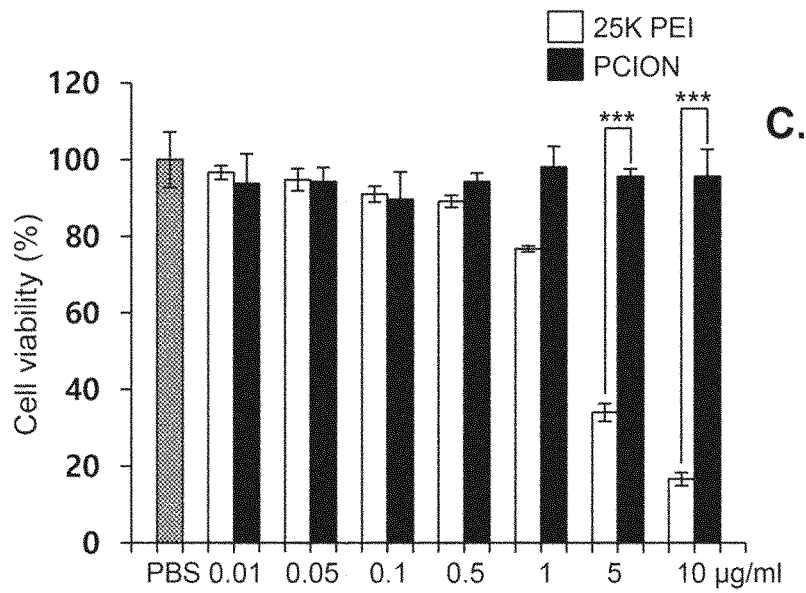
FIG. 1A illustrates cytotoxicity of PEG-coated, cross-linked, iron oxide nanoparticles (PCION), in which HeLa cells were treated with PBS, 25 kDa PEI, or PCION in the presence of a magnetic field (MGF) for 24 hours, cell viability thereof was measured by Cell Counting Kit-8 (CCK-8) assay 48 hours after treatment, results were normalized against PBS-only negative control cells, and each value was expressed as mean±SD of three independent experiments (n=3 per experiment)

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

According to an embodiment of the present disclosure, there is provided a complex including: (a) magnetic nanoparticles crosslinked with catechol grafted poly-L-lysine and having PEGylated surfaces; and (b) a virus.

The present disclosure also provides a method of enhancing transduction efficiency of a virus in a cell, including: administering the above-described complex to an individual; and (b) applying an external magnetic field (MGF) to the complex-administered individual.

The inventors of the present application have made intensive efforts to develop a composition for enhancing transduction efficiency of a virus in a cell. As a result, they verified that, when a composition, prepared by PEGylating a cross-linked product including magnetic nanoparticles and catechol grafted poly-L-lysine and binding a virus thereto, was used, transduction efficiency thereof in a cell was significantly increased by applying an external magnetic field thereto.

The term "magnetic nanoparticles" as used herein means magnetic field-responsive particles having a diameter of several nanometers to hundreds of nanometers, and the type of particle is not particularly limited so long as it can control movement characteristics in response to a magnetic field.

In one embodiment, the magnetic nanoparticles have a particle diameter of about 1 nm to about 200 nm. In a more specific embodiment, the magnetic nanoparticles have a particle diameter of about 1 nm to about 50 nm. In another embodiment, the magnetic nanoparticles have a particle diameter of about 1 nm to about 30 nm. In another embodiment, the magnetic nanoparticles have a particle diameter of about 1 nm to about 20 nm. In another embodiment, magnetic nanoparticles having a particle diameter of about 5 nm to about 15 nm may be used.

In one embodiment, the magnetic nanoparticles are preferably selected from the group consisting of maghemite ($Fe_2O_3$), magnetite ($Fe_3O_4$), and mixtures thereof.

The term "catechol-grafted poly-L-lysine" as used herein means a polymer in which a catechol functional group is grafted to poly-L-lysine. In one embodiment, poly-L-lysine (PLL)-3,4 dihydroxy-1-phenylalanine (DOPA), prepared through conjugation by chemical coupling between a primary amine group of PLL and a catechol functional group-providing compound, e.g., a carboxylic acid group of hydrocaffeic acid, may be used.

In one embodiment, PLL included in the catechol-grafted PLL may have a number average molecular weight of about $5 \times 10^2$ to about $3 \times 10^5$. For example, the number average molecular weight of PLL may range from about $1 \times 10^3$ to about $1 \times 10^5$, for example, from about $5 \times 10^3$ to about $5 \times 10^4$, for example, from about $1 \times 10^4$ to about $3 \times 10^4$. Grafting PLL with a catechol functional group as described above imparts strong binding strength between PLL and magnetic nanoparticles.

In one embodiment, in the catechol grafted poly-L-lysine, a degree of substitution of a catechol functional group with respect to PLL may range from about 5 to about 30. The term "a degree of substitution of a catechol functional group with respect to PLL" as used herein means the number of catechol functional groups bound per 100 L-lysine residues.

In one embodiment, the magnetic nanoparticles and the catechol grafted poly-L-lysine are mixed in a weight ratio of about 10:1 to about 1:5. In another embodiment, the weight ratio of the magnetic nanoparticles and the catechol grafted poly-L-lysine may range from about 5:1 to about 1:5, for example, from about 1:1 to about 1:5. The magnetic nanoparticles and the catechol grafted poly-L-lysine may be mixed and, more particularly, may be prepared by oil-in-water (O/W) single emulsion and evaporation. A detailed description of preparation methods will be described in Example 3 below. The term "crosslinking between magnetic nanoparticles and catechol grafted poly-L-lysine" as used herein means binding that can be formed by the above-described preparation method.

In one embodiment, a molar ratio of the magnetic nanoparticles to the virus may range from about 1:1 to about $1:5 \times 10^7$. The molar ratio may be appropriately selected according to type and properties of viruses, and is not particularly limited.

The term "PEGylation" as used herein refers to surface coating with polyethylene glycol, and residual amine groups on an exposed surface of the cross-linked magnetic nanoparticles and catechol grafted poly-L-lysine may be PEGylated by reacting with polyethylene glycol. The PEGylation of the complex extends a residence time of the magnetic nanoparticles in blood stream and reduces toxicity of the magnetic nanoparticles.

In the present specification, the magnetic nanoparticles cross-linked with catechol grafted poly-L-lysine and having PEGylated surfaces may be also referred to as PEGylated and cross-linked iron oxide nanoparticles (PCIONs).

According to another embodiment of the present disclosure, there is provided a method of treating cancer, including: (a) administering, to an individual, a complex including: (a) magnetic nanoparticles cross-linked with catechol grafted poly-L-lysine and having PEGylated surfaces; and (b) an antitumor virus.

The term "antitumor virus" as used herein refers to a viral vector for intracellular gene delivery, and is interpreted as including both replication-incompetent viruses commonly known in the art and all viral vectors specifically developed to be replication-competent in tumor cells. In the present specification, the term "adenovirus" described as an example may be simply referred to as "Ad" and, in particular, a replication-incompetent adenovirus may be referred to as "dAd". Adenoviruses are widely used as a gene delivery vector to obtain antitumor effects due to an intermediate sized genome, ease of manipulation, high titer, a wide range of target cells, and high infectivity. Both ends of the genome have about a 100 base pair (bp) to about 200 bp inverted terminal repeat (ITR), which is a cis-acting element necessary for DNA replication and packaging. The E1 region (E1A and E1B) of the genome encodes proteins responsible for the regulation of transcription and transcription of host cell genes. The E2 region (E2A and E2B) encodes proteins involved in viral DNA replication.

Among currently developed Ads, E1 region-deleted replication-incompetent Ads are widely used. Meanwhile, the E3 region is removed from a general Ad vector to provide a site into which a foreign gene is inserted (Thimmappaya, B. et al., Cell, 31:543-551(1982); and Riordan, J. R. et al., Science, 245:1066-1073(1989)). Thus, a foreign gene, used for exhibiting or enhancing antitumor effects of antitumor Ads, may be inserted into a deleted E1 region (E1A region and/or E1B region, preferably E1B region) or a deleted E3 region, more preferably, into a deleted E3 region. In addition, a foreign gene sequence may also be inserted into a deleted E4 region. The term "deletion" as used herein with regard to viral genomic sequences means that the corresponding sequence is completely or partially deleted, or is mutated.

In addition, Ad can package total DNA up to about 105% of the wild type genome, and thus further package about 2 kb of DNA (Ghosh-Choudhury et al., EMBO J., 6:1733-1739(1987)). Thus, the above-described foreign gene sequence inserted into Ad may be further bound to the Ad genome.

Ads have 42 different serotypes and A to F subgroups. Among these, Ad type 5 belonging to the subgroup C is the most desired starting material to obtain an Ad vector according to the present disclosure. Biochemical and genetic information on Ad type 5 is well known. Foreign genes delivered by Ad are replicated in the same manner as in episome, and thus have very low genetic toxicity against host cells. Thus, genetic treatment using Ad according to the present disclosure is determined as being very safe.

According to the present disclosure, other viruses may be used in addition to the Ad. Non-limiting examples of the viruses used include, but are not limited to, vaccinia virus (Puhlmann M. et al., Human Gene Therapy 10:649-657 (1999)), a lentivirus (Wang G et al., J. Clin. Invest. 104(11): R55-62(1999)), and a herpes simplex virus (Chamber R., et al., Proc. Natl. Acad. Sci USA 92:1411-1415(1995)).

According to the most exemplary embodiment, the virus according to the present disclosure has a promoter-targeted nucleotide sequence-poly A sequence, and the promoter-targeted nucleotide sequence-poly A sequence may be inserted into a deleted E1 (E1A region and/or E1B region, preferably E1B region) or E3 region, preferably a deleted E3 region. In addition, the virus may be expressed by a bicistronic expression system, such as promoter-first targeted nucleotide sequence-poly A sequence-internal ribosome entry site (IRES)-second targeted nucleotide sequence-poly A sequence, in which the first targeted nucleotide and the second targeted nucleotide are linked to each other by IRES or the 2A system.

Antitumor viruses are known to infect cells via the coxsackievirus and adenovirus receptor (CAR). In brain cancer cells, head and neck cancer cells, melanoma cells, bladder cancer cells, and the like, however, an expression level of CAR is low, which is an obstacle to tumor treatment using an antitumor virus. In cells with a high expression level of CAR, increasing infection rates of antitumor viruses is a great help for cancer treatment.

The present disclosure is aimed to overcome challenges of cancer treatment. For example, when the composition according to the present disclosure is used under external magnetic field application conditions, a CAR-independent antitumor virus may be transduced into a cell. The application of an external magnetic field, according to the present disclosure, means a local magnetic field formation for a tumor cell to which a virus is to be delivered, and more particularly, means the application of magnetic force in a direction in which the composition according to the present disclosure is directed to a tumor cell.

The content of a paper describing magnetofection (Kazumasa et al. Biomaterials (30):1809-1814(2009), Jonathan et al, Journal of Clinical Neuroscience 19:875-880(2012)), with regard to the application of magnetic field according to the present disclosure, is incorporated herein by reference. According to the present disclosure, the foreign gene sequence to be delivered by an antitumor virus into a cell is a cancer treatment gene that induces the death of cancer cells and ultimately degenerates tumors. Examples of the cancer treatment gene include, but are not limited to, tumor suppressor genes, immunomodulatory genes [e.g., cytokine genes, chemokine genes, and costimulatory factors (auxiliary molecules necessary for T cell activation, such as B7.1 and B7.2)], antigenic genes, suicide genes, cytotoxic genes, cell proliferation inhibitory genes, pro-apoptotic genes, and anti-angiogenic genes.

A suicide gene is a nucleic acid sequence that expresses a substance for inducing a cell to be easily killed by an external factor or induces toxic conditions in a cell. A gene well-known as such a suicide gene is the thymidine kinase (TK) gene (U.S. Pat. Nos. 5,631,236 and 5,601,818). TK gene product-expressing cells are susceptible to selective killing by administration of gancyclovir. In addition, CD gene product-expressing cells are susceptible to selective killing by administration of 5-FC. A tumor suppressor gene refers to a gene encoding a polypeptide that inhibits tumorigenesis. The tumor suppressor gene is a naturally occurring gene in mammals, and the deletion or inactivation of this gene is believed to be a prerequisite for tumorigenesis. Examples of suitable tumor suppressor genes include APC, DPC4/Smad4, NF-1, NF-2, MTS1, WT1, BRCA1, BRCA2, VHL, p53, Rb, MMAC-1, MMSC-2, retinoblastoma genes (Lee et al. *Nature,* 329:642(1987)), the adenomatous polyposis coli protein: U.S. Pat. No. 5,783,666), the nasopharyngeal carcinoma tumor suppressor gene that is located on chromosome 3p21.3 (Cheng et al. *Proc. Nat. Acad. Sci.,* 95:3042-3047(1998)), deleted colon carcinoma (DCC) genes, MTS1, CDK4, VHL, p110Rb, and members of the INK4 family of tumor suppressor genes including p16 and p21 and therapeutically effective fragments thereof (e.g., p56Rb, p94Rb, and the like). It will be understood by one of ordinary skill in the art that other known antitumor genes, in addition to the above-listed genes, may be used.

The term "antigenic gene" as used herein refers to a nucleotide sequence which is expressed in target cells to produce cell-surface antigenic proteins that can be identified in an immune system. Examples of such antigenic genes include carcinoembryonic antigens (CEAs), prostate specific antigens (PSAs), HER-2, the α-fetoprotein (AFP), and p53 (WO 94/02167). To easily identify the antigenic gene by the immune system, the antigenic gene may be bound to a MHC I-type antigen.

The term "cytotoxic gene" as used herein refers to a nucleotide sequence exhibiting toxic effects through expression in a cell. Examples of the cytotoxic genes include nucleotide sequences encoding *Pseudomonas* exotoxin, ricin toxin, diphtheria toxin, and the like.

The term "cytostatic gene" as used herein refers to a nucleotide sequence which is expressed in cells to stop a cell cycle during the same. Examples of such cytostatic genes include, but are not limited to, p21, retinoblastoma genes, E2F-Rb-fused protein genes, cyclin-dependent kinase inhibitor-coding genes (e.g., p16, p15, p18, and p19), growth arrest specific homeobox (GAX) genes (WO 97/16459 and WO 96/30385).

In addition, a variety of therapeutic genes useful in treating various diseases may be carried by a virus of the present disclosure as a means of helping the antitumor effect. Examples of the therapeutic genes include genes encoding cytokines (e.g., interferon-α, interferon-β, interferon-γ and interferon-δ), interleukins (e.g., IL-1, IL-2, IL-4, IL-6, IL-7, IL-10, IL-12, IL-19, IL-20, and IL-23), and colony-stimulating factors (e.g., GM-CSF and G-CSF), chemokine group (monocyte chemotactic protein 1 (MCP-1), monocyte chemotactic protein 2 (MCP-2), monocyte chemotactic protein 3 (MCP-3)), monocyte chemotactic protein 4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), an EBI1-ligand chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), an eotaxin, I-309, human protein HCC-1/NCC-2, human protein HCC-3, and mouse protein C10. In addition, the therapeutic genes include genes encoding tissue-type plasminogen activator (tPA) or urokinase, and LAL-generating genes to provide sustained thrombolysis for preventing hypercholesterolemia. Moreover, many polynucleotides, available for treatment of various diseases including cystic fibrosis, adenosine deaminase deficiency, AIDS virus, and malignant and inflammatory diseases and conditions, are known.

The term "pro-apoptotic gene" as used herein refers to a nucleotide sequence expressed, resulting in programmed cell death. Examples of suitable pro-apoptotic genes include p53, adenovirus E3-11.6K (derived from Ad2 and Ad45) or adenovirus E3-10.5K (derived from Ad), an adenovirus E4 gene, Fas ligand, TNF-α, TRAIL, p53 pathway genes, and genes encoding caspases.

The term "anti-angiogenic gene" as used herein refers to a nucleotide sequence expressed, resulting in the extracellular secretion of anti-angiogenic factors. Non-limiting examples of anti-angiogenic factors include angiostatin, inhibitors of vascular endothelial growth factor (VEGF) such as Tie 2 (PNAS, 1998, 95, 8795-8800), endostatin, and VEGFtrap.

In addition, relaxin genes or the decorin gene, identified by the inventors of the present disclosure as being suitable for adenovirus gene treatment, is also a gene that may be delivered into cells by a gene carrier.

The above-described nucleotide sequences may be available from a DNA sequence databank such as GenBank or EMBL.

According to the present disclosure, binding between magnetic nanoparticles or a cross-linked product and an antitumor virus is attributed to positive charge property of a surface of the cross-linked product and negative charge property of the virus. After PEGylation of the surface of the cross-linked product, the virus may bind to remaining positively charged surface portions, and a plurality of viruses and a plurality of PEGylated cross-linked products may bind to each other, thereby forming an aggregate.

In one embodiment, a molar ratio of the magnetic nanoparticles to the antitumor virus may range from about 1:1 to about $1:5 \times 10^7$. The molar ratio may be appropriately selected according to the type and characteristics of an antitumor virus, and is not particularly limited.

In one embodiment, the composition according to the present disclosure has enhanced introduction into a target tumor cell by application of an external MGF. As described in examples below, when the composition according to the present disclosure is injected by application of an external MGF, the efficiency of viral transfer into a tumor cell may be significantly improved CAR-independently. This means that a virus-induced antitumor effect is significantly increased. Such an increase in antitumor effects is observed both in replication-competent recombinant viruses and replication-incompetent recombinant viruses.

To induce an effective antitumor effect using a virus, it is necessary to induce an effective cell death effect through more rapid proliferation of a virus and spreading thereof to neighboring cells as compared to cancer cells that grow at a high rate. In addition, for successful cancer gene therapy using a virus, methods which enhance safety as well exhibit high treatment effects should be developed. The combined administration of aprotic polar solvents developed in the present disclosure significantly increases the rate of intracellular infection of a virus and thus remarkably increases an antitumor effect. Consequently, the dose of a virus required for cancer treatment may be decreased and thus in vivo toxicity and an immune response to the virus may be greatly decreased.

In one embodiment, the complex of the present disclosure exhibits decreased liver tropism by application of an external MGF. The term "liver tropism" as used herein refers to a characteristic inherent to general cationic polymers and naked viruses, in which a cationic polymer or naked virus introduced into the body moves to mainly the liver. When the complex of the present disclosure is used, a tumor-to-liver uptake ratio is increased 450-fold through magnetically-guided delivery by an external MGF, as compared to when the external MGF is not applied.

In one embodiment, the cancer may be selected from the group consisting of laryngeal cancer, pancreatic cancer, lung cancer, non-small cell lung cancer, colon cancer, bone cancer, skin cancer, head or neck cancer, ovarian cancer, uterine cancer, rectal cancer, stomach cancer, anal cancer, breast cancer, fallopian tube cancer, endometrial cancer, cervical cancer, vaginal cancer, vulvar cancer, Hodgkin's disease, esophageal cancer, intestinal tumors, endocrine gland cancer, thyroid cancer, parathyroid cancer, adrenal cancer, soft-tissue sarcoma, urethral cancer, penile cancer, prostate cancer, chronic or acute leukemia, lymphocytic lymphoma, bladder cancer, renal or ureteral cancer, renal cell carcinoma, renal pelvic carcinoma, central nervous system (CNS) tumors, primary CNS tumors, spinal cord tumors, hepatic cancer, bronchial cancer, nasopharyngeal cancer, and brainstem glioma or pituitary adenoma. The virus included in the composition of the present disclosure exhibits efficacy with respect to killing various tumor cells, and thus may be used for the treatment of a variety of tumor-related diseases or disorders, e.g., the above-listed various cancers. The term "treatment" as used herein means: (i) prevention of tumorigenesis; (ii) suppression of tumor-related diseases or disorders associated with the removal of tumor cells; and (iii) alleviation of tumor-related diseases or disorders associated with the removal of tumor cells. Thus, the term "therapeutically effective amount" as used herein refers to an amount sufficient to achieve the pharmacological effects described above.

In one embodiment, the tumor of the present disclosure is a virus receptor (CAR)-negative tumor. When a virus is delivered using the composition of the present disclosure by applying a magnetic field, the virus may be transduced into a cell without going through the known CAR pathway, and thus may be also efficiently applied to CAR-negative tumors. However, this means that the virus may also be applied to CAR-negative tumors, and it is obvious that the virus may also be applied to CAR-positive tumors. In the case of CAR-negative tumors, intracellular transduction rate of the virus is very low, and thus may be significantly increased by magnetofection using the composition of the present disclosure, this means that the composition of the present disclosure may be effectively applied to, in particular, CAR-negative tumors.

The pharmaceutical composition of the present disclosure includes a pharmaceutically acceptable carrier, in addition to active ingredients. The pharmaceutically acceptable carrier, which is commonly used in formulation, may be lactose, dextrose, sucrose, sorbitol, mannitol, starch, acacia gum, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but the present disclosure is not limited to the above examples. The pharmaceutical composition may further include, in addition to the above-described components, a lubricant, a wetting agent, a sweetener, a flavor enhancer, an emulsifying agent, a suspension agent, a preservative, or the like. Suitable pharmaceutically acceptable carriers and formulations are described in detail in Remington's Pharmaceutical Sciences (19th ed., 1995).

The pharmaceutical composition of the present disclosure may be administered parenterally, for example, administered intravenously, intraperitoneally, intramuscularly, subcutaneously, or locally when an external magnetic field is applied. In another embodiment, after the above-described administration, the composition of the present disclosure may be guided to be introduced into a tumor cell by applying an external magnetic field. In particular, the composition of the present disclosure may be administered by intraperitoneal injection in ovarian cancer, by portal injection in liver cancer, by direct injection into a tumor mass in breast cancer, by direct injection as an enema in colon cancer, and by direct injection into a catheter in bladder cancer.

A suitable dose of the pharmaceutical composition of the present disclosure may depend on many factors, such as formulation methods, administration methods, patient age, body weight, gender, pathologic conditions, diet, administration time, administration route, excretion speed, and reaction sensitivity. Ordinarily skilled doctors can easily determine and prescribe an effective dose for targeted treatment. Generally, the pharmaceutical composition of the preset disclosure includes about $1 \times 10^5$ pfu/ml to about $1 \times 10^{15}$ pfu/ml of a recombinant virus, and, in general, $1 \times 10^{10}$ pfu/ml thereof may be administered by injection every two days for two weeks. However, the suitable dose may be appropriately adjusted in consideration of the above-described various factors.

The pharmaceutical composition of the present disclosure may be formulated using a pharmaceutically acceptable carrier and/or an additive by a method, which may be easily carried out by one of ordinary skill in the art to which the present disclosure pertains, to be prepared in a unit dose form or to be contained in a multi-dose container. The formulation may be a solution in oil or an aqueous medium, a suspension, an emulsion, an extract, powder, granules, a tablet, or a capsule, and may further include a dispersing or stabilizing agent.

The pharmaceutical composition of the present disclosure may be used alone, but also may be used in combination with other commonly used chemotherapy or radiotherapy, and the combined therapy may more effectively treat cancer. Non-limiting examples of suitable chemotherapeutic agents used together with the composition of the present disclosure include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastine, and methotrexate. Suitable radiotherapy used together with the composition of the present disclosure may be X-ray radiation, γ-ray radiation, or the like.

Hereinafter, the present disclosure will be described in further detail with reference to the following examples. It is obvious to one of ordinary skill in the art that these examples are provided only for illustrative purposes, and are not intended to limit the scope of the present disclosure.

EXAMPLES

Test Materials and Methods

Example 1: Cell Culture and Ad Preparation

All cancer cell lines (Hela, U343, A549, SK-BR3, MCF7, and B16F10) were cultured in Dulbecco's Modified Eagle Medium (DMEM; Gibco-BRL, Grand Island, N.Y.) supplemented with 10% fetal bovine serum (FBS; Gibco-BRL) at 37° C. in a humidified atmosphere containing 5% $CO_2$. A human cervical cancer cell line (HaLa), brain cancer cell line (U343), lung cancer cell line (A549), breast cancer cell lines (SK-BR3 and MCF7), embryonic kidney cell line (HEK-293), and a mouse melanoma cancer cell line (B16F10) were purchased from the American Type Culture Collection. Magnetofection-mediated in vitro Ad gene delivery efficiency was tested using a GFP-expressing replication-incompetent Ad (dAd). HmT is a firefly luciferase-expressing oncolytic Ad that replicates under the control of a cancer-specific modified TERT promoter and a hypoxia-responsive element. Ads were propagated in HEK-293 cells and purified by CsCl gradient centrifugation. Viral particles (VP) were enumerated using optical density measurements at 260 nm, where 1 absorbency unit ($OD_{260}=1$) equaled $1.1 \times 10^{12}$ VP/ml. Purified viruses were stored at −80° C. until use.

Example 2: Experimental Materials

Methoxy poly(ethylene glycol)-succinimidyl-succinate (mPEG-SS, MW 2000) was purchased from SunBio, Inc. 1-ethyl-3-(3-dimethylaminopropyl)-carbodiimide hydrochloride was purchased from Tokyo Chemical Industry Co., Ltd. Poly-L-lysine hydrobromide (PLL, MW 25,000), hydrocaffeic acid, and rhodamine B isothiocyanate (MW 536.08) were obtained from Sigma Aldrich. The Cell Counting Kit-8 (CCK-8) was purchased from Dojindo Molecular Technologies, Inc. Dialysis membranes were obtained from Spectrum Laboratories, Inc. DMEM, RPMI 1640 medium, Dulbecco's phosphate-buffered saline (PBS), FBS, penicillin/streptomycin, and trypsin were obtained from Gibco-BRL. Iron oxide nanoparticles having a diameter of 10 nm or less were obtained from the National Creative Research Initiative Center for Oxide Nanocrystalline Materials and School of Chemical and Biological Engineering at Seoul National University.

Example 3: Synthesis of PEGylated and Cross-Linked Iron Oxide Nanoparticles (PCIONs)

Catechol-grafted PLL (PLL-DN) polymers were synthesized by chemical coupling of a carboxylic acid group from hydrocaffeic acid to a primary amine group of PLL. A reaction was allowed to slowly occur between 65 mg (350 mmol) of EDC dissolved in 2 ml of methanol and 2 ml of a DMF solution containing 55.2 mg (350 mmol) of hydrocaffeic acid. The reaction product was added to 100 mg (4 mmol) of PLL dispersed in 2 ml of methanol, and then the resulting solution was stirred at room temperature for 12 hours. The polymer was dialyzed against an HCl solution (pH 4) with a dialysis membrane (Mw cutoff of 3000) for 2 days, and then lyophilized under reduced pressure. The chemical structure and the degree of substitution of catechol groups were evaluated by $^1$H-NMR spectroscopy (Brucker DRX 400 spectrometer operating at 400 MHz).

Cross-linked iron oxide nanoparticles (CIONs) were synthesized by an oil-in-water (O/W) single emulsion and evaporation method. To increase the stability of iron oxide nanoparticles, 1 ml of a chloroform solution including 2 mg of oleic acid-coated iron oxide nanoparticles was added to 20 mg of PLL-DN dispersed in 10 ml of deionized water. Simultaneously, to apply O/W emulsion, mixing was performed for 5 minutes through a tip-type Branson sonifier with a duty cycle of 30 and an output of 3. The organic solvent was evaporated under reduced pressure, and then the uncombined PLL-DN polymer and the remaining solvent were removed by ultrafiltration using the Amicon Ultra-4 centrifugal filter (Mw cutoff of 100 kDa. For synthesis of PEGylated CIONs (PCIONs), a reaction was allowed to occur between 2 mg of the purified CIONs and 200 µg of mPEG-SS (Mw 2000) dissolved in 1 ml of deionized water, and then the resulting solution was purified using the Amicon Ultra-4 centrifugal filter (Mw cutoff of 100 kDa) to remove a residual mPEG-SS polymer. In addition, rhodamine-labeled PCIONs were prepared by conjugation between 200 µg of PCIONs and 2 µg of rhodamine B isothiocyanate dispersed in 200 µl of DMSO. After reacting for 24 hours, the resulting product was washed through several times of dispersion in deionized water and centrifugation.

Example 4: Evaluation of in Vitro Cell Viability and Intracellular Uptake of PCIONs To identify the toxicity of PCIONs, HeLa cells were distributed into a 96-well plate ($1\times10^4$ cells/well) supplemented with 10% (v/v) FBS at 37° C. for 24 hours prior to a transfection experiment. The HeLa cells were transfected with 25 kDa PEI- or PCION-containing DMEM having a concentration of 0.01 µg/ml to 10 µg/ml for 1 day by using an external magnetic field. After 48 hours, cell viability was evaluated by CCK-8 analysis according to the manufacturer's instructions, and was compared with that of untreated cells.

To visualize intracellular uptake of PCIONs, rhodamine-conjugated PCIONs (PCION-rhodamine) were transfected into HeLa cells ($1\times10^5$ cells/well) in a 4-chamber tissue culture slide. The cells were cultured for 15 minutes in the presence or absence of a permanent magnet (MagnetoFACTOR plate; chemicell GmbH) having a field strength of 70 mT to 250 mT and a gradient of 50 T m$^{-1}$ to 130 T m$^{-1}$. The treated cells were washed twice with a PBS solution and fixed with a 1% formaldehyde/PBS solution for 30 minutes, and the cells were observed using a confocal laser scanning microscope (LSM510; Carl Zeiss Meditec AG). For iron staining, U343, MCF7, and B16F10 cells were distributed into a 24-well plate at a concentration of $5\times10^4$ cells/well 24 hours before treatment. Thereafter, the cells were treated with 5 µg/ml of PCIONs for 15 minutes with or without exposure to a permanent magnet (MagnetoFACTOR plate). The PCION-treated cells were washed twice with PBS and evaluated using an iron staining kit (HT-20, Sigma Aldrich).

Example 5: Physicochemical Characterization of Ad-PCION Complexes

To prepare Ad-PCION complexes, Ad particles ($2\times10^{10}$ VP/PBS, pH 7.4) were mixed with various concentrations of PCION polymers. As a result, a ratio of PCIONs to Ad particles was $2\times10^5$, $5\times10^5$, $2\times10^6$, and $5\times10^6$. Before use, a solution was maintained at room temperature for 30 minutes to induce a reaction.

The hydrodynamic diameter and surface charge of a dAd-PCION complex ($5\times10^6$ molar ratio) were measured by a dynamic light scattering instrument (Zeta-Plus) equipped with a He—Ne laser at a wavelength of 632 nm. To test colloidal stability thereof in PBS, the size of the dAd-PCION complex was measured for 7 days (day 0, day 1, day 3, or day 7). Additionally, the size and morphology of the dAd-PCION complex were observed by transmission electron microscopy (TEM) (The FBI Tecnai™ F20).

Example 6: Transduction Efficiency of Ad-PCION Complex

Transduction efficiency of dAds or dAd-PCION complexes, with or without an MGF, were measured by quantifying GFP expression by fluorescence-activated cell sorting (FACS) analysis in CAR-positive A549, U343, CAR-negative MCF7, and B16F10 cells. Each cell line was distributed into wells ($5\times10^4$ cells/well) in a 24-well plate 24 hours before infection. The cells were transfected with naked dAds or dAd-PCION complexes at a multiplicity of infection of 10 (A549, U343, and SK-BR3 cells) or 100 (MCF7 and B16F10 cells) with or without an MGF for 15 minutes, and then media were replaced with new media containing 5% FBS. 24 hours after transduction, the cells were observed using a fluorescence microscope (Olympus IX81; Olympus Optical). The cells were also observed by a BD FACScan analyzer (Becton-Dickinson Biosciences) using CellQuest software (Becton-Dickinson). Data from 10,000 trials was collected for additional analysis, and relative fluorescence intensities were shown.

Example 7: Serum Stability Test

To examine an effect of serum on transduction efficiency, a GFP-expressing Ad uncomplexed with PCION (dAd) and a GFP-expressing Ad complexed with PCION (dAd-PCION) were incubated in the presence or absence of human serum at 37° C. for 45 minutes. A549 cells ($5\times10^4$ cells/well) were incubated with a naked dAd or dAd-PCION complex at 20 MOI for 24 hours (dAd) or 15 minutes in the presence of an MGF (dAd-PCION), and then media were replaced with new media containing 5% FBS. 24 hours after transduction, the cells were observed using a fluorescence microscope (Olympus IX81). The cells were also observed by a BD FACScan analyzer (Becton-Dickinson) using CellQuest software (Becton-Dickinson). Data from 10,000 trials was collected for additional analysis, and relative fluorescence intensities were shown.

Example 8: Evaluation of Interaction Between Ad-PCION Complex and Cell Membrane by TEM Imaging U343 cells were distributed into wells ($5\times10^4$ cells/well) in a 24-well plate for 24 hours. Subsequently, the cells were treated with PBS, naked dAd (100 MOI), PCION (100 MOI), or dAd-PCION (100 MOI) in the presence of an MGF, and dAd-PCION (100 MOI) in the absence of an MGF, for 15 minutes. The cells were washed with PBS, fixed in a cacodylate buffer (0.1 M) containing 3% glutaraldehyde and 2% formaldehyde, and processed for TEM. An RMC MT-6000 XL microtome was used to collect 90 nm-thickness sections. The cell sections were visualized and captured with a JEM-2000EX II TEM (JEPL; Nikon Corp.).

Example 9: MTT Assay

To evaluate a cancer cell killing effect of HmT or HmT-PCION with or without an MGF, U343, SK-BR3, MCF7, B16F10, and C33A cells were cultured in a 24-well plate. When reaching a confluence of 50%, the cells were infected with naked HmT or HmT-PCION (2 or 5 MOI for A549, U343, SK-BR3, and C33A cells, and 50 or 200 MOI for MCF7 and B16F10 cells) for 15 minutes in the presence or absence of an MGF. After injection, media were replaced with 5% FBS-containing media, and the cells were incubated at 37° C. 2 days after infection, 200 μl (2 mg/ml in PBS) of 3-(4,5-dimethylthiazol-2-yl)-2,5-diphenyl-tetrazolium bromide (MTT; Sigma Aldrich) was added to each well and incubated at 37° C. for 4 hours. Thereafter, the supernatant was removed, and the precipitate was dissolved in 1.0 ml of dimethylsulfoxide. Then, the plates were read on a microplate reader at 540 nm. PBS-treated cells were simultaneously analyzed as a negative control.

Example 10: In Vivo Antitumor Efficacy

To measure an antitumor effect of HmT and HmT-PCION, $1\times10^7$ of MCF7 xenograft tumor cells were subcutaneously injected into abdomens of 6- to 8-week-old female athymic nude mice (Charles River Korea Inc.) in the presence or absence of an MGF. After the tumor cells reached a volume of 100 mm³ to 120 mm³, the mice were randomly divided into four groups, and were intratumorally injected with 30 μl of PBS by using an MGF, HmT ($5\times10^{10}$ VP) with an MGF, or HmT-PCION ($5\times10^{10}$ VP) with or without an MGF. The growth of the tumor was measured using a caliper every two days after treatment. The length (L) and width (W) of the tumor were measured, and the volume of the tumor was calculated by the following equation:
Volume of tumor=$0.523$ LW².

Example 11: Histological and Immunohistochemical Analysis

PBS with an MGF, HmT ($5\times10^{10}$ VP) with an MGF, or HmT-PCION ($5\times10^{10}$ VP) with or without an MGF was intratumorally injected and, 72 hours after injection, MCF7 tumor tissues were obtained. The obtained tumor tissues were fixed in 10% formalin and paraffin-embedded, and 5 μm sections were stained with hematoxylin and eosin and analyzed using a microscope. The tumor sections were also stained with an anti-mouse proliferating cell nuclear antigen (PCNA, available from DaKo) which indicates tumor cell proliferation or an anti-E1A (Santa Cruz Biotechnology) antibody which indicates Ad replication in tumors. Immunohistochemical sections were counterstained with Mayer's hematoxylin.

Example 12: In Vivo Whole Body Bioluminescence Imaging

When the volume of an MCF7 tumor reached about 150 mm³ to 200 mm³, tumor-bearing mice were intratumorally injected with PBS with an MGF, HmT ($5\times10^{10}$ VP) with an MGF, or HmT-PCION ($5\times10^{10}$ VP) with or without an MGF. 45 hours after treatment, bioluminescence imaging was performed. The mice were anesthetized in a chamber filled with 2% isoflurane in oxygen and D-luciferine (150 mg/kg; Caliper Life Science Inc.), and photographic and luminescent images were obtained using an IVIS II imaging system (Caliper Life Science). In vivo bioluminescence signals were calculated as the sum of supine and prone acquisitions for each mouse after background extraction (photon flux/sec) from whole body sites of interest.

Example 13: Statistical Analysis

The data was expressed as mean±standard deviation (SD). Statistical comparison was performed using StarView software (SAS Institute) and a Mann-Whitney nonparametric test. The criterion for defining statistical significance was $P<0.05$.

Experimental Results

1. Preparation and Characterization of PCION Cluster

PEGylated magnetite nanoparticle clusters (PCIONs) were prepared as known in the art. Briefly, poly-L-lysine (PLL)-3,4 dihydroxy-1-phenylalanine (DOPA) was synthesized by conjugating branched PLL with DOPA via 1-ethyl-3-(3-dimethylaminopropyl)carbodiimide coupling chemistry between primary amine groups of branched PLL and a carboxylic acid group of hydrocaffeic acid. The degree of substitution of catechol groups with respect to PLL was 17. CCK-8 analysis was used to measure the inherent toxicity of the produced PCION, with 25 kDa PEI used as a positive control (see FIG. 1A). Cytotoxicity was not shown over various ranges of PCION concentrations from 0.01 μg/ml to 10 μg/ml, even at the highest concentration of PCION. In striking contrast, it was confirmed that, when cells were treated with 10 μg/ml of 25 kDa PEI, cell viability was significantly decreased by 16.5%, and the 25 kDa PEI exhibited significant toxicity. Previous studies have shown that high molecular weight compounds including many cationic amine groups, e.g., branched PLL, induce cytotoxicity by inhibiting cell membrane biological functions. The main role of cationic amine groups on cytotoxicity has been known, and it is assumed that low PCION cytotoxicity is attributed to a decrease in free amines at surfaces of PCIONs due to their conjugation with DOPA and PEG.

2. Effect of MGF on Cellular Uptake Efficiency of PCIONs

To examine the magnetism of the produced PCIONs, confocal microscopic analysis using PCION-rhodamine in the presence or absence of an MGF was performed. Cells were also observed using an optical microscope after iron staining. HeLa cells were treated with PCION-rhodamine in the presence or absence of an MGF for 15 minutes, and one hour later, the cells were visualized with a fluorescence microscope (see FIG. 1B). The cells treated with PCION-rhodamine in the presence of an MGF exhibited a sufficient cellular uptake of PCION-rhodamine, while the uptake of rhodamine was not observed in the cells treated with PCION-rhodamine in the absence of an MGF. Similar uptake patterns were observed in the iron-stained cells (see FIG. 1C). Unrecognizable iron traces were observed in three cancer cell lines treated with PCION in the absence of an MGF. In clear contrast, clear and recognizable blue iron stains were observed in all the cancer cell lines treated with PCION in the presence of an MGF. These results indicate that an MGF significantly increases a cellular uptake of a magnetic nanomaterial, e.g., PCION, and coincide with previous magnetofection studies.

3. Physicochemical Properties of Ad-PCION Complexes

Figure 2A:
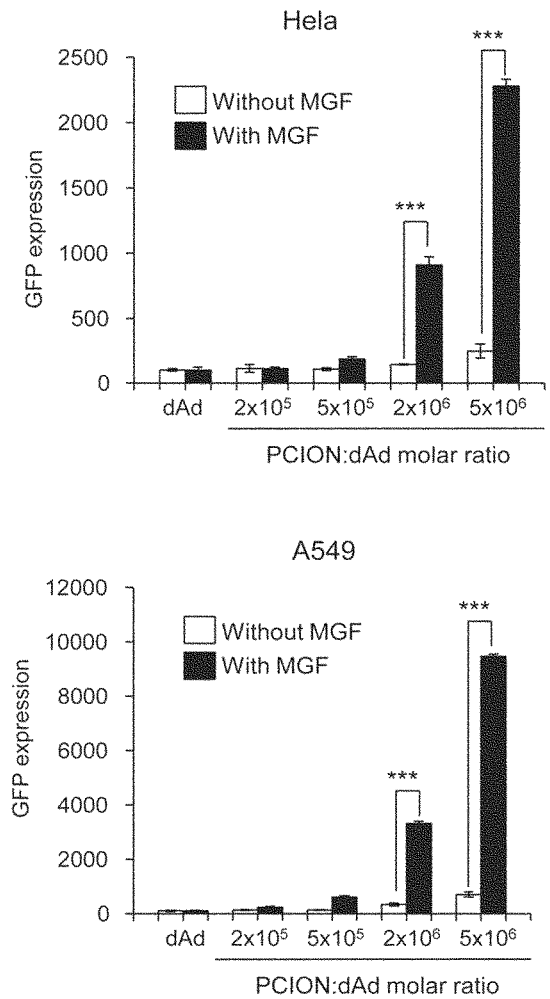
FIG. 2A illustrates transduction efficiency of dAd or dAd-PCION complexes ($2\times10^5$, $5\times10^5$, $2\times10^6$, or $5\times10^6$ molar ratios of PCION polymer:dAd particles) with or without an MGF, in which the transduction efficiency was measured by GFP expression, results represent mean GFP expression (arbitrary fluorescence units)±SD of three experiments, and ***P<0.001 versus dAd-PCION without an MGF.

To optimize formulation of Ad-PCION complexes, GFP-expressing replication-incompetent Ads (dAds) were complexed with PCION at various molar concentrations, and GFP analysis was performed thereon in the presence or absence of an MGF (see FIG. 2A). In HeLa cells, GFP expression was increased in a dose (molar ratio)-dependent manner in both in the presence and absence of an MGF. However, the HeLa cells treated in the presence of an MGF exhibited a greater increase in GFP expression and showed 6.4-fold and 9.3-fold increases at molar ratios of PCION polymer to Ad particles of $2\times10^6$ and $5\times10^6$, respectively, as compared to the HeLa cells treated without an MGF ($P<0.001$ in both comparisons). A549 cells exhibited similar results and showed 9.8-fold and 13.4-fold increases at molar ratios of PCION polymer to Ad particles of $2\times10^6$ and $5\times10^6$, respectively, as compared to A549 cells treated without an MGF ($P<0.001$ in both comparisons). The data indicates that complexation with PCION significantly increases an Ad delivery efficiency, in particular, in the presence of an MGF. Additionally, an experiment was performed at molar ratios of PCION polymer to Ad particles of greater than $5 \times 10^6$, but further delivery efficiency improvement or cellular uptake was not observed. Based on these results, a molar ratio of PCION to Ad particles of $5 \times 10^6$ was selected and used to produce dAd-PCION complexes.

Figure 2B:
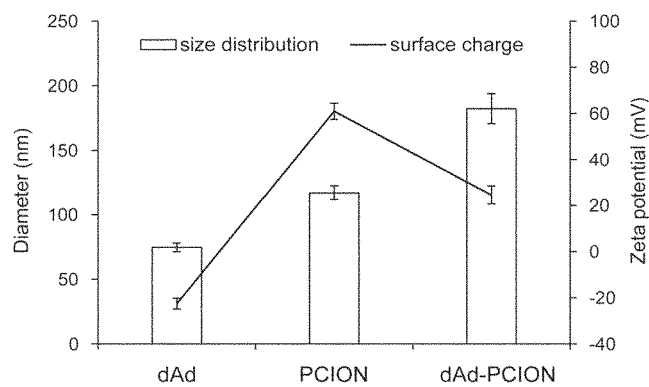
FIG. 2B illustrates average size distribution and zeta potential of naked dAd and dAd-PCION complexes, in which sizes and charges were measured as mean±SD of five independent experiments.
Figure 2C:
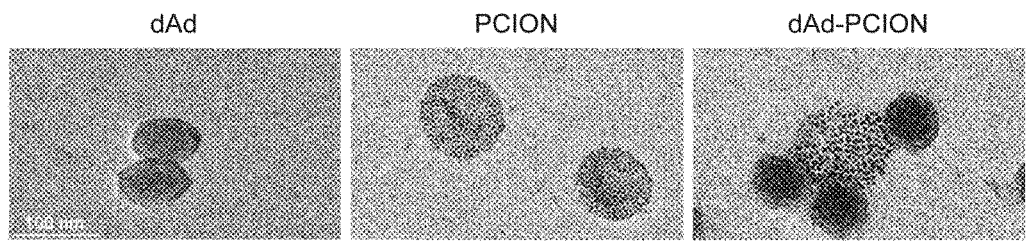
FIG. 2C illustrates transmission electron microscopy (TEM) images of dAd, PCION, or a dAd-PCION complex ($5\times10^6$ PCION polymer:dAd particle molar ratio) in PBS (pH 7.4)
Figure 2D:
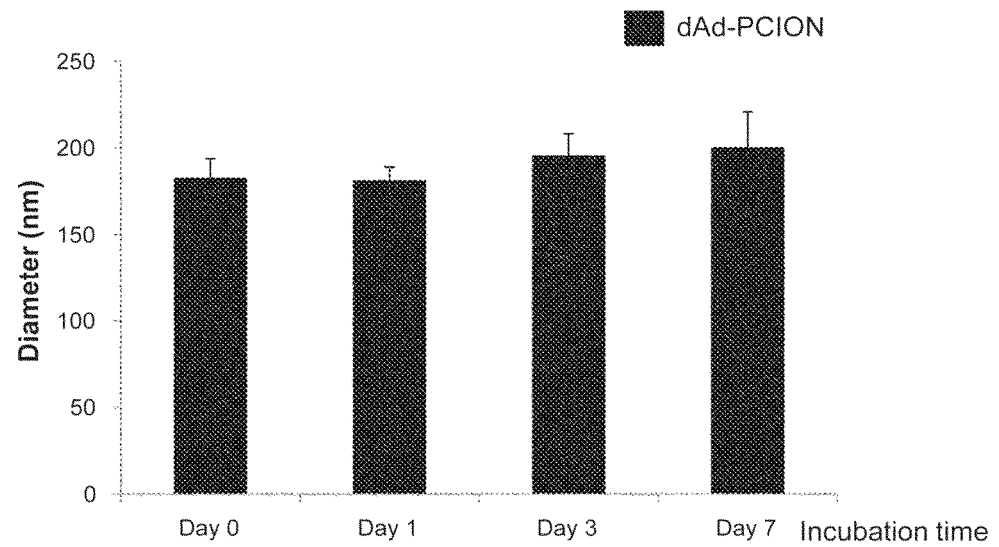
FIG. 2D illustrates colloidal stability of a dAd-PCION ($5\times10^6$ PCION polymer:dAd particle molar ratio) complex, in which an average size of the dAd-PCION complex was measured in PBS up to 7 days and the sizes were measured as mean±SD of five independent experiments.

The size, surface charge, and morphology of the optimized dAd-PCION formulation was characterized by dynamic light scattering (DLS), zeta potential, and TEM, respectively. As expected, the size of the dAd-PCION complexes was 182.3 nm, which was much larger than that of naked Ad (74.6 nm) or PCIONs (117.1 nm) (see FIG. 2B). The surface charge of the dAd-PCION complexes was 24.6 mV, which was far higher than that of naked dAd (−22.6 mV), but was lower than that of PCION (60.9 mV), which indicates that the dAd-PCION complexes were satisfactorily produced. The decreased surface charge of dAd-PCIONs as compared with PCIONs may be attributed to strong electrostatic interactions between cationic PCION and an anionic Ad surface, and enables formation of a polyelectrolyte complex. TEM images of dE1/GFP(dAd), PCION, and dAd-PCION were obtained (see FIG. 2C). The results of the TEM images coincide with DLS and zeta potential data of the present disclosure, from which it is confirmed that dAd-PCION complexes had a much greater diameter than that of naked dAd or PCION, which demonstrates physical binding between naked dAd and PCION into successfully formed dAd-PCION complexes. In addition, the colloidal stability of dAd-PCION in a PBS buffer was measured. As illustrated in FIG. 2D, Ad complexed with PCION exhibits good colloidal stability over a period of 7 days.

Surface modification of Ad with a polymer such as PEG may inhibit specific Ad fiber/target cell receptor interactions and reduces delivery efficiency of the above complexes. However, a positive zeta potential of 24.6 mV for dAd-PCION complexes was obtained, and dAd-PCION was expected to successfully enter cells by compatible interactions with an anionic cell membrane. Overall, these results demonstrate optimal formation of dAd-PCION complexes using a molar ratio of PCION polymer to Ad particles of $5 \times 10^6$, and the polyelectrolyte complex was expected to efficiently enter cells, especially when an MGF was applied.

4. Enhanced Transduction Efficiency of Ad-PCION Complexes by Applying MGF

To visually compare the transduction efficiency of dAd with that of dAd-PCION, various cancer cell lines were treated under five experimental conditions: transduction using dAd for 24 hours; transduction using dAD+/−MGF for 15 minutes; and transduction using dAD-PCION+/−MGF for 15 minutes (see FIG. 3). 24 hours after transduction, GFP expression levels of all the groups were measured. As expected, the expression of GFP was not observed in CAR-negative cells (MDF7 and B16F10), while cells transduced with dAd for 24 hours exhibited GFP expression in CAR-positive cells (A549, U343, and SK-BR3), and the CAR-dependent cell entry mechanism of naked Ad was identified. As a result of transduction of naked Ad for 15 minutes in the presence or absence of an MGF, no detectable GFP expression was observed in the above cell lines, which indicates that 15 minutes are not sufficient for naked Ad transduction to occur.

In clear contrast to this, all cells transduced with dAd-PCION complexes in the presence of an MGF for 15 minutes induced significantly higher GFP expression than that under any other treatment condition (P<0.001). The fluorescence level of cancer cells treated with dAd-PCION in the presence of an MGF was quantitated by FACS analysis. Due to this treatment, A549, U343, SK-BR3, MCF7, and B16F10 cells exhibited 28-, 30-, 20-, 32-, and 141-fold increases in GFP expression, respectively as compared to GFP expression levels observed in the case of transduction with dAd-PCION in the absence of an MGF. Transduction with dAd-PCION for 15 minutes in the absence of an MGF exhibited greater vector uptake than transduction with naked dAd, and the positive surface charge of dAd-PCION enables higher uptake efficiency than CAR-mediated endocytosis. In addition, due to the presence of an MGF, cellular uptake of dAd-PCION into all tested cancer cells was greatly increased. These results were consistent with previous findings, and application of an MGF increased cellular uptake of a magnetic nanomaterial into target cells. In summary, the results indicate that the remarkably increased GFP expression in all the cell lines tested in the present disclosure was caused by magnetically triggered, rapid cellular uptake of a dAd-PCION vector.

Figure 3A:
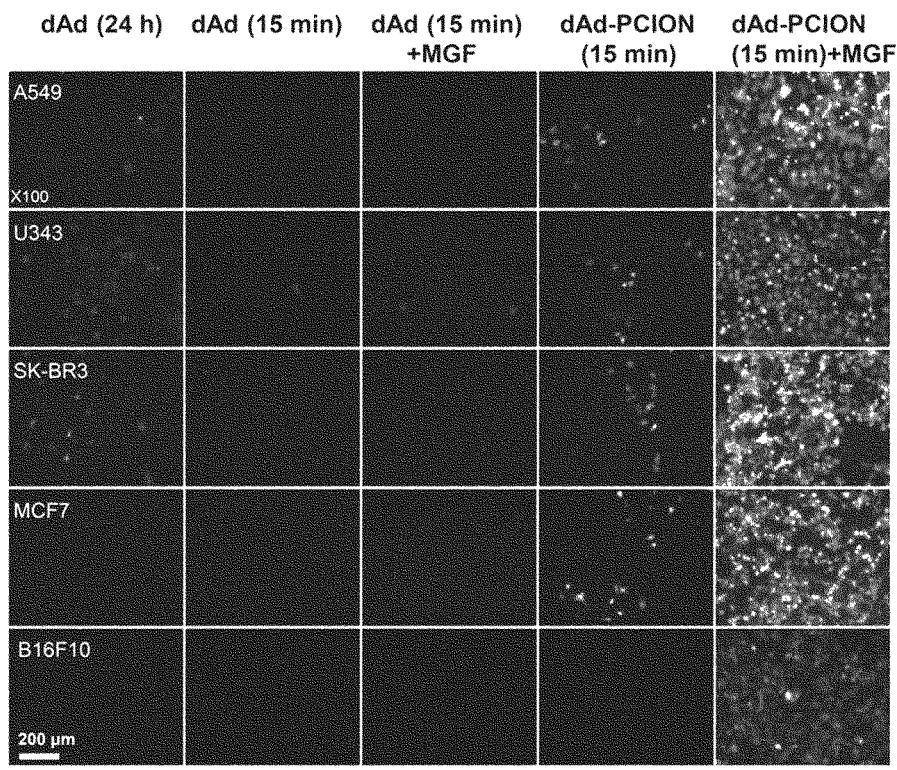
FIG. 3A illustrates transduction efficiency of naked dAd and dAd-PCION with or without an MGF in cancer cell lines A549, U343, SK-BR3, MCF7, and B16F10 cells, in which cell lines A549, U343, and SK-BR3 were transduced at an MOI of 10, cell lines MCF7 and B16F10 used 100 MOI, representative fluorescence microscopy images of transduced cells (dAd-PCIONs generated using a $5\times10^6$ molar ratio of PCION polymer:dAd particles) are shown, and the original magnification is 100×.
Figure 3B:
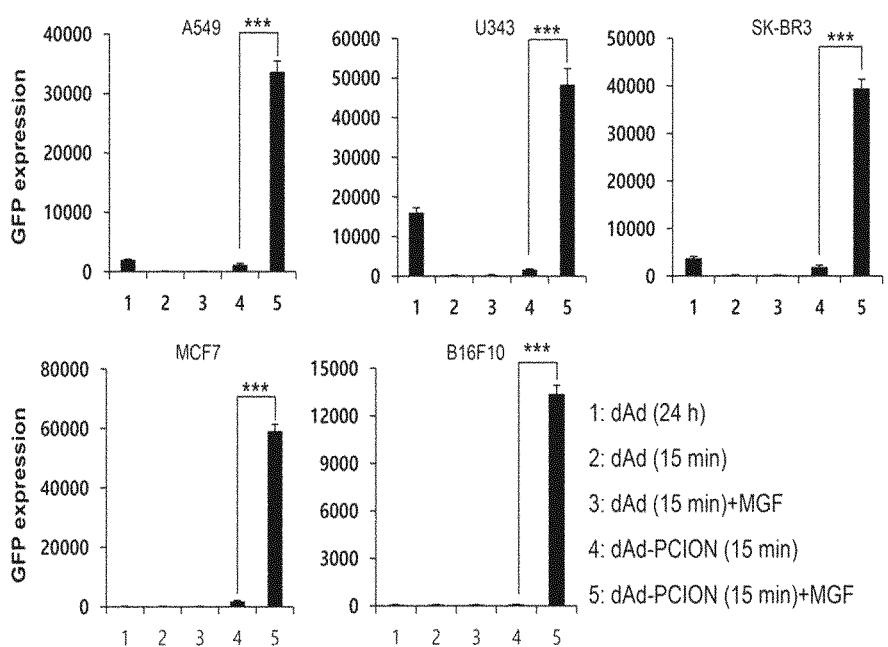
FIG. 3B illustrates GFP expression measured by flow cytometry, in which results represent mean±SD of three independent experiments, and ***P<0.001 versus dAd-PCION without an MGF.
Figure 3C:
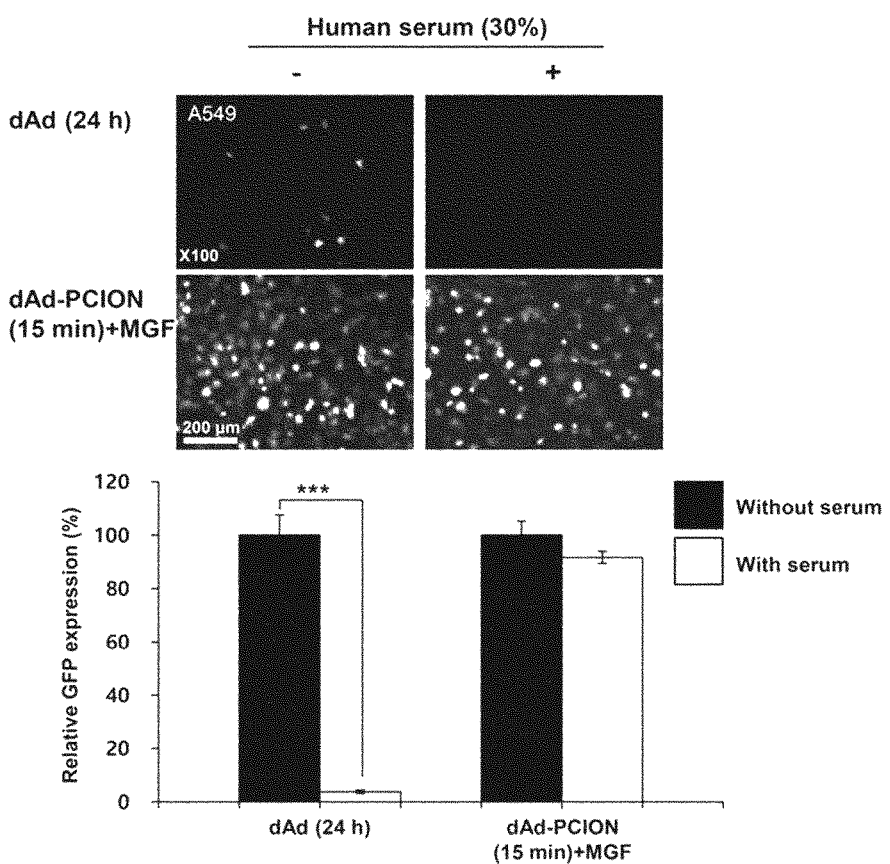
FIG. 3C illustrates a transduction study of naked dAd and dAd-PCION with or without 30% human serum, in which after incubation of dAd and dAd-PCION with or without serum for 45 minutes, A549 cells were transduced with naked dAd or a dAd-PCION complex for 24 hours (dAd) or 15 minutes (dAd-PCION) in the presence of an MGF, the cells were observed using a fluorescence microscope 24 hours after transduction, the original magnification is 100×, results represent mean±SD of three experiments, and ***P<0.001 versus dAd without serum.

Due to electrostatic affinity between positively charged complexes and negatively charged serum proteins, serum proteins may have a considerable impact on transduction efficiency of gene vectors. Thus, the stability of dAd-PCION in 30% human serum was measured. Naked dAd or dAd-PCION was incubated at 37° C. for 45 minutes with or without serum, and then A549 cells were treated with dAd or dAd-PCION in the presence of an MGF. As illustrated in FIG. 3C, serum reduced transduction efficiency of naked dAd by 3.8%, demonstrating that naked Ad can be easily inactivated by serum. In clear contrast to this, dAd-PCION-treated cells exhibited a similar GFP expression level in the presence of an MGF regardless of the amount of human serum. These results indicate that complexation of Ad with PCION can protect the activity of Ad against serum.

Figure 1B:
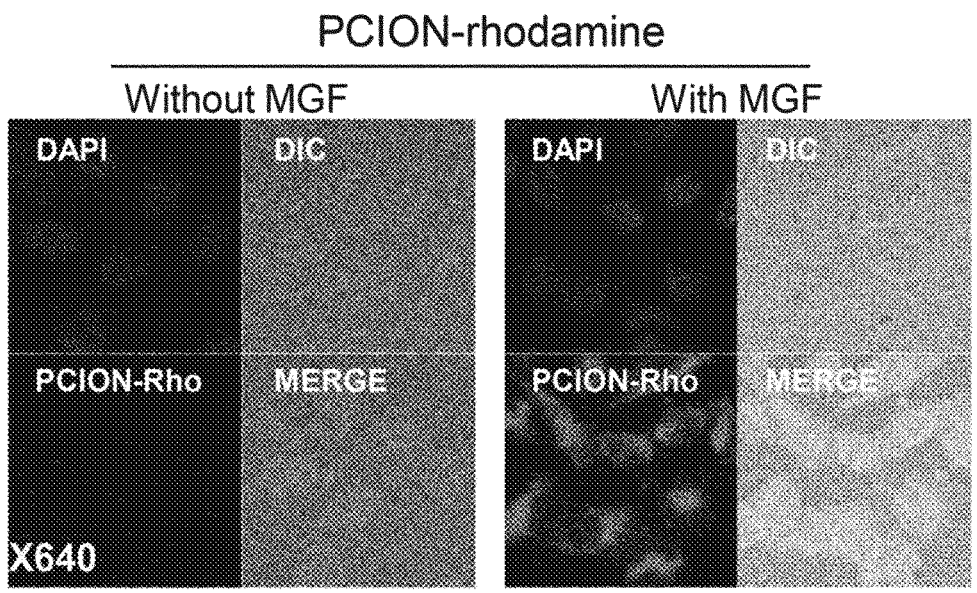
FIG. 1B illustrates cellular uptake of rhodamine-labeled PCION into HeLa cells with or without an MGF, in which nuclei were stained with DAPI and DIC denotes differential interference contrast.
Figure 1C:
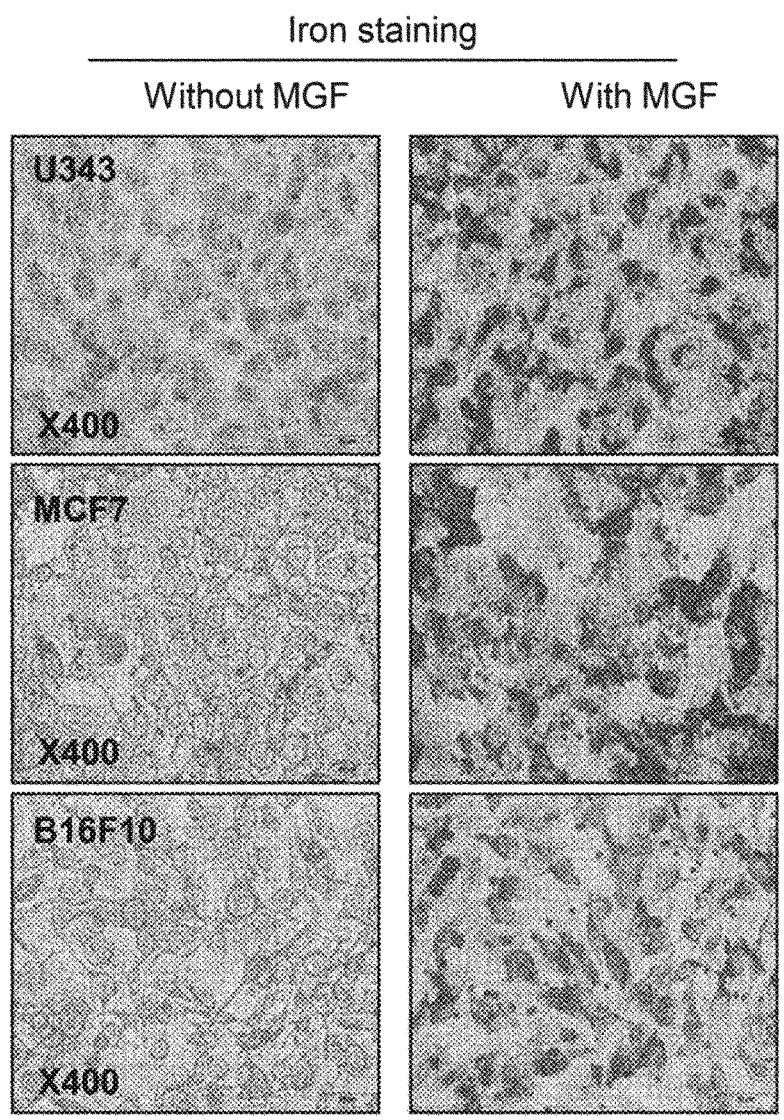
FIG. 1C illustrates staining results of U343, MCF7 and B16F10 cells treated with PCION with or without an MGF for 15 minutes and washed with PBS, by using an iron staining kit.
Figure 4:
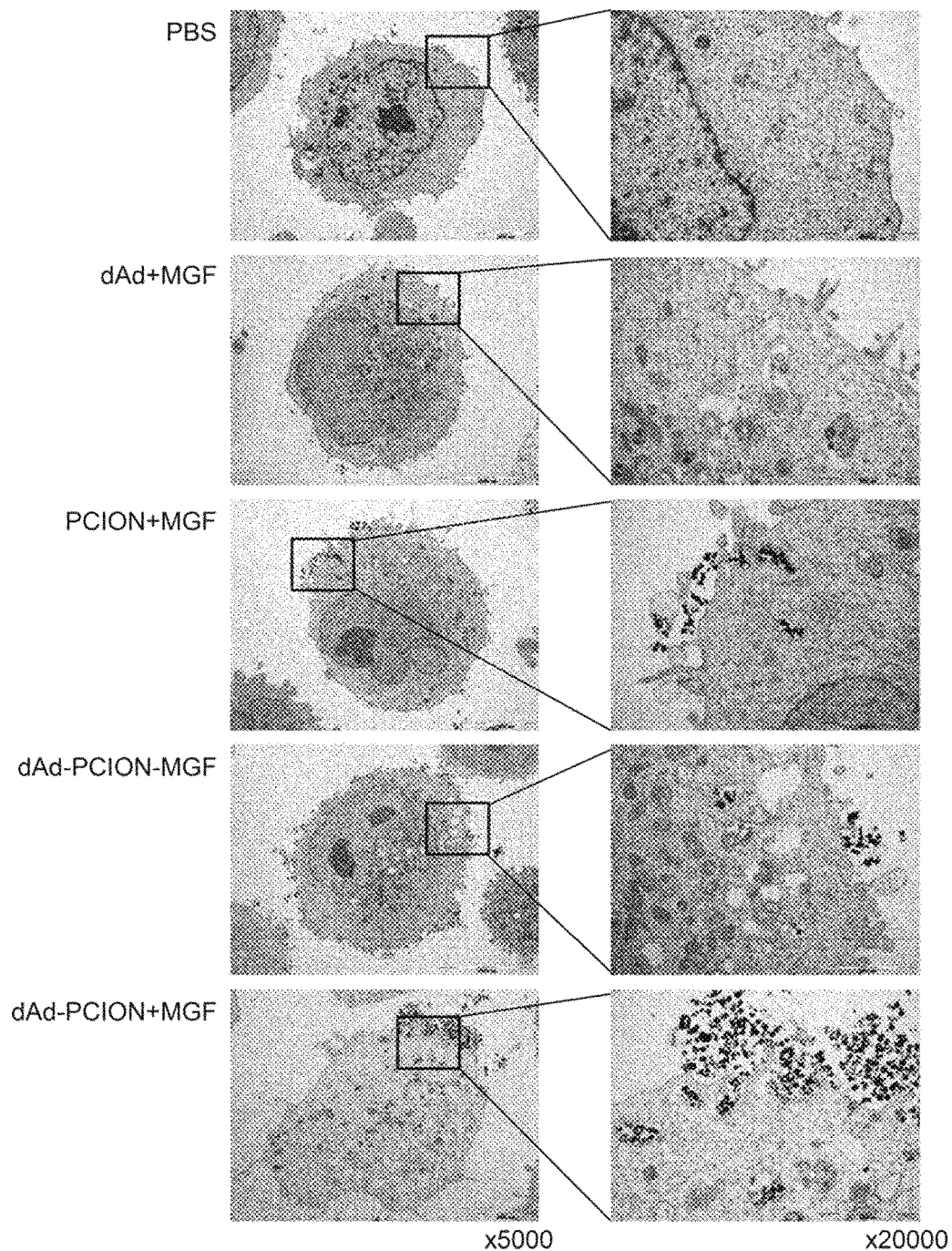
FIG. 4 illustrates TEM images of cellular uptake of dAd, PCION, or dAd-PCION in the presence of an MGF, together with PBS and dAd-PCION as controls in the absence of an MGF, in which U343 cells were treated with dAd, PCION, or a dAd-PCION complex (100 MOI each) and analyzed by TEM after 15 minutes, and data shown represents three independent experiments, and the original magnifications are 5000× and 20000×.

To further examine the increased transduction efficiency of dAd-PCION in the presence of an MGF, TEM imaging research was performed. U343 cells were treated with PBS, naked dAd (100 MOI) with an MGF, PCION with an MGF, or dAd-PCION (100 MOI) with or without an MGF. 15 minutes after treatment, TEM images were obtained (see FIG. 4). As expected, no visible intracellular Ad particles was observed in treatment with PBS or dAd at both magnifications of 5000× and 20000×. Occasional electron-dense particles were observed intracellularly in treatment with PCION by application of an MGF, and cellular uptake results are shown in FIGS. 1B and 1C. When cells were treated with dAd-PCION particles without an MGF, as illustrated in FIG. 3, a greater number of particles were detected near the inside of cells and cell membranes than in treatment with naked dAd. In clear contrast to this, treatment with dAd-PCION in the presence of an MGF resulted in a great number of conjugated virus particles observed inside cells, which indicates enhanced cellular uptake of dAd-PCION for 15 minutes. From GFP and TEM results, it was confirmed that magnetofection-mediated dAd-PCION cellular uptake is more efficient and rapid than in CAR-mediated endocytosis of naked Ad.

Figure 5A:
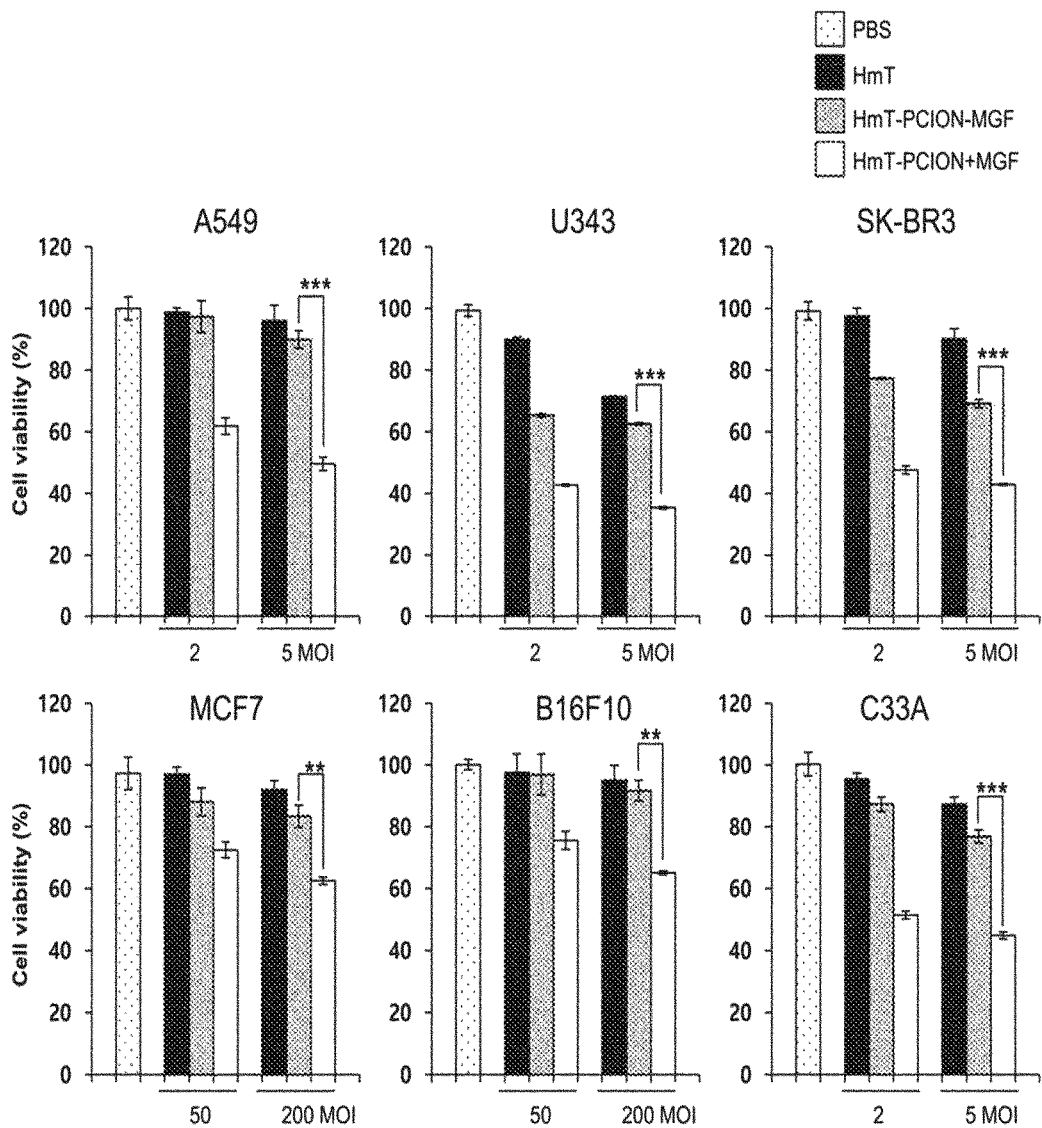
FIG. 5A illustrates a cancer cell killing effect of HmT or HmT-PICON with or without an MGF, in which cells were infected with HmT or HmT-PCION at an MOI of 2 or 5 for A549, U343, SK-BR3, and C33A cells, and at an MOI of 200 for MCF7 and B16F10 cells, cell viability was measured by MTT assay 48 hours after infection, data represents mean±SD of three experiments, P<0.01, and *P<0.001.

5. Enhanced Antitumor Effect of Ad-PCION Complexes by Application of an MGF and Intracellular Viral Replication To examine a cancer cell killing effect of magnetofection-mediated oncolytic Ad (HmT)-PCION complexes, MTT analysis was performed on A549, U343, SK-BR3, MCF7, B16F10, and C33A cells transduced for 15 minutes in the presence or absence of an MGF (see FIG. 5A). The HmT oncolytic Ad has 6 copies of a hypoxia-responsive element (HRE) and a modified hTERT promoter in its E1A region, and thus viral replication is regulated under the HRE-hTERT hybrid promoter. In addition, HmT contains the firefly luciferase gene in its E3 region, allowing in vivo luciferase visualization as an indicator of intracellular replication. HmT-infected groups exhibit minimal antitumor effects, which coincides with the GFP expression results (see FIG. 3) showing that 15 minutes are not sufficient for naked Ad to enter cancer cells. Cancer cell killing efficacy was slowly increased as compared to naked HmT when HmT oncolytic Ad was complexed with PCION in the absence of an MGF, showing an increase in cancer cell killing of 6.1% (A549), 8.7% (U343), 21.0% (SK-BR3), 8.7% (MCF7), 3.3% (B16F10), and 10.4% (C33A). This indicates that accelerated oncolytic Ad cellular uptake was mediated by positively charged PCION particles. The HmT-PCION complexes in the presence of an MGF induced enhanced cancer cell killing efficacy as compared to both naked HmT and HmT-PCION in the absence of an MGF. In particular, the cancer cell killing efficacy was increased 12.9-fold, 2.3-fold, 5.8-fold, 4.7-fold, 7.0-fold, and 4.3-fold in A549, U343, SK-BR3, MCF7, B16F10, and C33A cells, respectively as compared to naked oncolytic Ad ($P<0.01$ in all cell lines). As a result of cytotoxicity analysis of PCION alone, cytotoxicity was not shown up to 10 μg (see FIG. 1A), and these results indicate that the enhanced cell killing effect of the HmT-PCION complexes in the presence of an MGF was attributed to the cytotoxicity of HmT alone. This also indicates that PCION acts as a magnetically active vehicle that enables cellular uptake of an HmT vector without inhibiting the oncolytic activity of HmT.

Figure 5B:
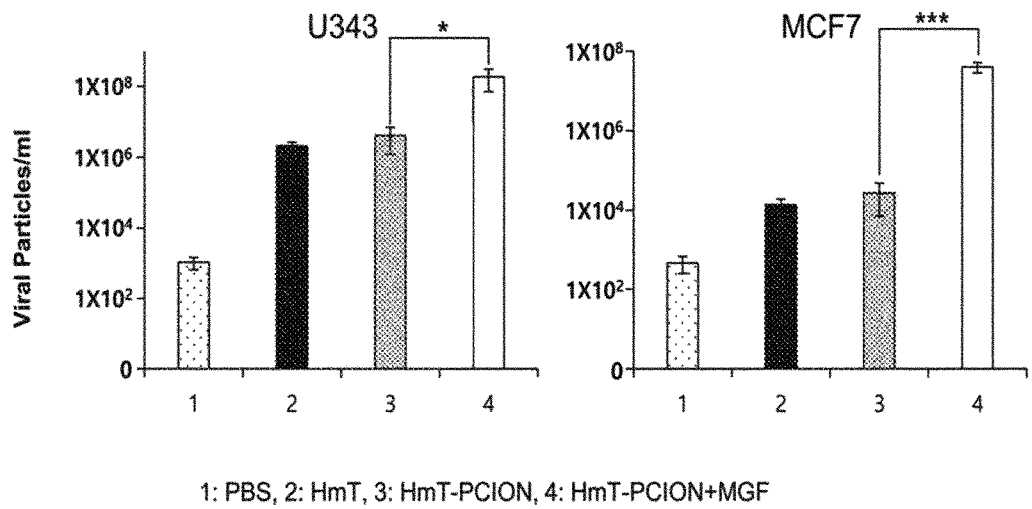
FIG. 5B illustrates viral production of HmT or HmT-PCION with or without an MGF, in which U343 and MCF7 cells were infected with HmT or HmT-PCION with or without an MGF at an MOI of 5 and 500 for U343 and MCF7, respectively, after 2 days, a total viral yield in cell lysates was measured by quantitative PCR, data represents mean±SD of three experiments, *P<0.05, and ***P<0.001.

A correlation between HmT viral progeny production and the cancer cell killing effect was studied by viral production analysis. U343 and MCF7 cells were treated with PBS, HmT, or an HmT-PCION complex in the presence or absence of an MGF for 15 minutes, and media were replaced with new media. Three days later, the viral progeny produced from the treated cells were measured by quantitative PCR. As illustrated in FIG. 5B, viral production had a positive correlation with the cancer cell killing effect of naked HmT or HmT-PCION in the presence or absence of an MGF (see FIG. 5A). In particular, HmT-PCION complex-infected U343 cells in the presence of an MGF produced 89- and 46-fold higher viral titers, respectively as compared to HmT-treated U343 cells and HmT-PCION complex-treated U343 cells in the absence of an MGF ($P<0.05$ in all comparisons). MCF7 cells infected with HmT-PCION complexes in the presence of an MGF exhibited 2910-fold and 1468-fold higher viral production than the cases of HmT and HmT-PCION, respectively in the absence of an MGF ($P<0.001$ in all comparisons). From the data, it is confirmed that transfection with HmT-PCION using an MGF significantly enhanced antitumor effects as compared to transfection with naked HmT or HmT-PCION in the absence of an MGF. The results demonstrate that the enhanced cancer cell killing effect obtained from the transfection with HmT-PCION using an MGF is attributed to enhanced uptake, efficient viral replication, and potential subsequent antitumor effects.

Figure 6A:
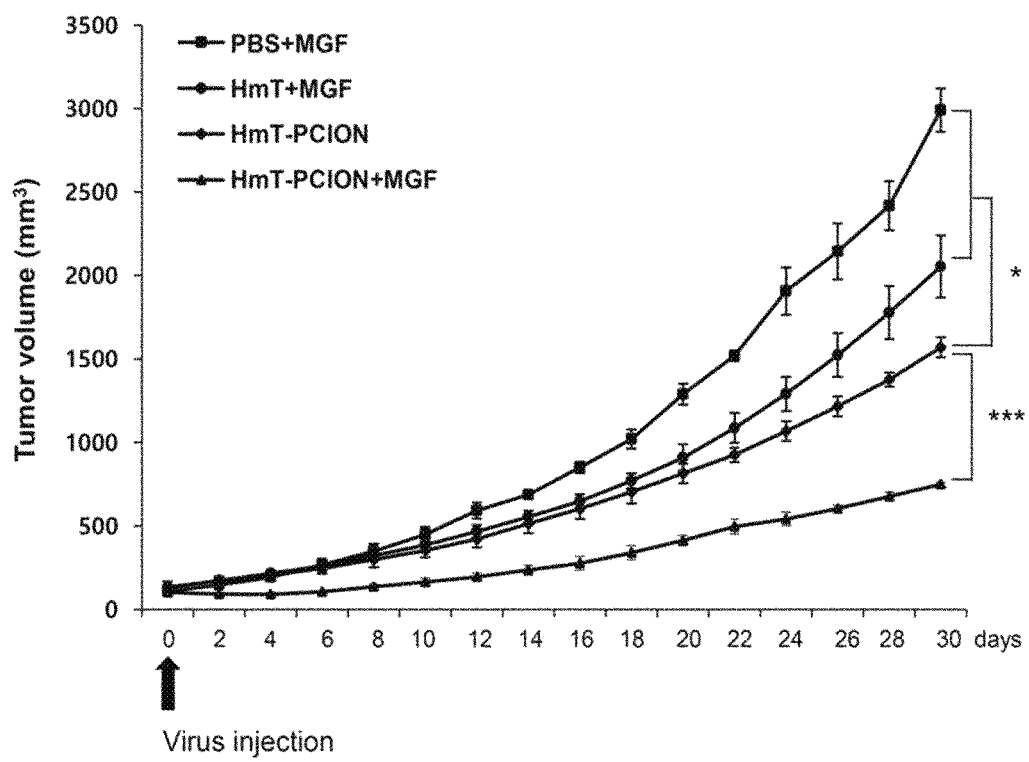
FIG. 6A illustrates antitumor efficacy of HmT and HmT-PCION complexes with or without an MGF, in which MCF7 tumors were xenografted subcutaneously into nude mice, when a tumor size reached 100 mm$^3$ to 120 mm$^3$, mice were treated with PBS with an MGF, HmT with an MGF, or HmT-PCION with or without an MGF by single intratumoral injection, N=6 mice/group, data represents mean±SD, and *P<0.05, HmT-PCION without an MGF versus PBS or HmT with an MGF and ***P<0.001, HmT-PCION with an MGF versus HmT-PCION without an MGF at 30 days after treatment.

6. Enhanced Therapeutic Efficacy of Oncolytic Ad-PCION Complex Transduction by Application of MGF Magnetofection enhancement of in vivo therapeutic efficacy of oncolytic Ad was examined in a murine MCF7-tumor xenograft model. When the size of a tumor reached 100 mm³ to 120 mm³, mice were intratumorally injected with PBS using an MGF, HmT using an MGF, or HmT-PCION using or without using an MGF. After the treatment, the volume of the tumor was measured (see FIG. 6A). To exclude the possibility of enhanced antitumor efficacy mediated by a magnetofection process, magnetofecion was performed on all groups except for an HmT-PCION non-MGF control. As consistent with the gene delivery efficiency data shown in FIG. 3, naked HmT did not induce significant antitumor efficacy due to low infection efficiency of naked Ad in CAR-negative MCF7 cancer cells. As consistent with the in vitro results of the present disclosure, HmT-PCION complex-treated mice without an MGF delayed tumor growth more efficiently as compared to PBS or naked HmT ($P<0.05$). Mice treated with HmT-PCION using an MGF exhibited a more efficient decrease in tumor growth than all other groups. Injection of HmT-PCION by application of an MGF resulted in 3.9-fold, 2,7-fold, and 2.1-fold higher therapeutic efficacy as compared to the cases of PBS using an MGF, naked HmT using an MGF, and HmT-PCION without an MGF, respectively ($P<0.001$). Such a remarkable decrease in tumor growth is attributed to tumor-specific antitumor effects mediated by efficient replication of HmT in tumor tissues after efficient infection with PCION in the presence of an MGF.

Figure 6B:
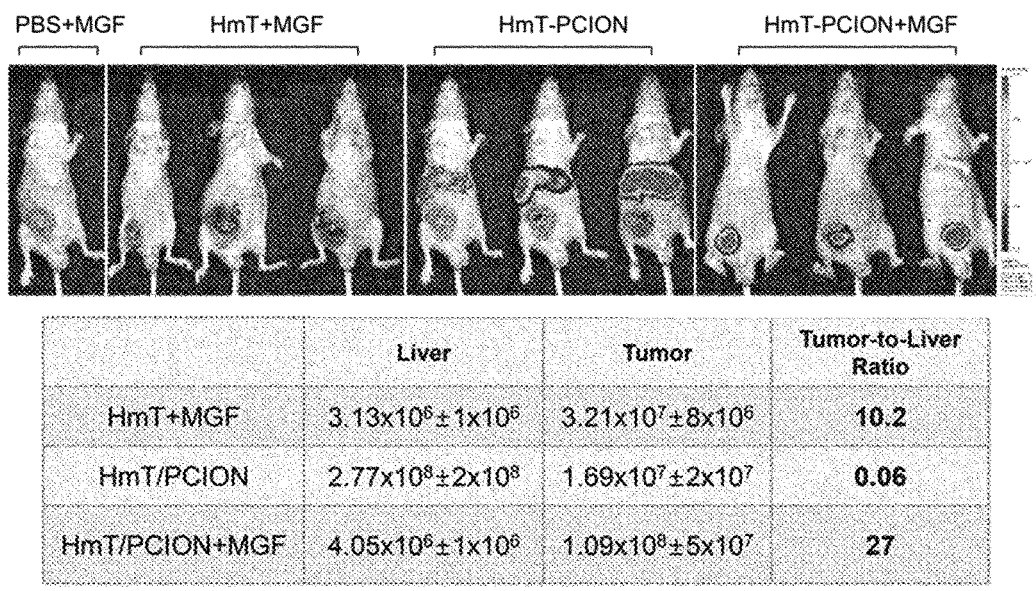
FIG. 6B illustrates bioluminescence whole-body imaging of MCF7 tumor-bearing mice, in which mice with subcutaneous MCF7 xenograft tumors were injected intratumorally with PBS with an MGF, HmT with an MGF, or HmT-PCION with or without an MGF, in which bioluminescence imaging was performed 48 hours after treatment, and an average optical signal intensity is expressed as photons acquired per second in regions of interest.

Previous studies showed significant liver tropism of PLL- and PEI-based cationic polymers in biodistribution studies. To gain insight on in vivo mobility of an HmT-PCION complex, IVIS whole-body luciferase analysis was performed to track the movement of HmT-PCION in a MCF7 tumor-bearing mouse model after treatment with PBS using an MGF, HmT using an MGF, or HmT-PCION with or without an MGF (see FIG. 6B). The PBS-treated tumor-bearing mice did not exhibit luciferase activity. Mice intratumorally treated with naked HmT in the presence of an MGF produced modest luciferase signals mostly localized on only the tumor. In contrast, mice treated with HmT-PCION in the absence of an MGF showed strong luciferase signals in liver tissues with minimal expression of luciferase in tumor tissues, and earlier findings of non-specific liver uptake of PLL-based cationic polymers were confirmed. Contrary to these results, HmT-PCION injected by application of an MGF into local tumor sites induced strong luciferase expression in tumor tissues without non-specific luciferase expression in the liver. These results clearly indicate that site-specific magnetically-guided nanoparticles can overcome the potential risk of non-specific liver tropism inherent in general cationic polymers. In mice treated with an HmT-PCION complex using an MGF, a ratio of luciferase signals of tumor to liver, which is a major aspect of treatment efficacy and safety, was increased 450-fold compared to mice treated with HmT-PCION without an MGF. Thus, this approach provides significant improvement in safer and more efficacious Ad-cationic polymer complex-based cancer gene therapy in combination with magnetofection.

7. Histological and Immunohistological Analysis

Figure 7:
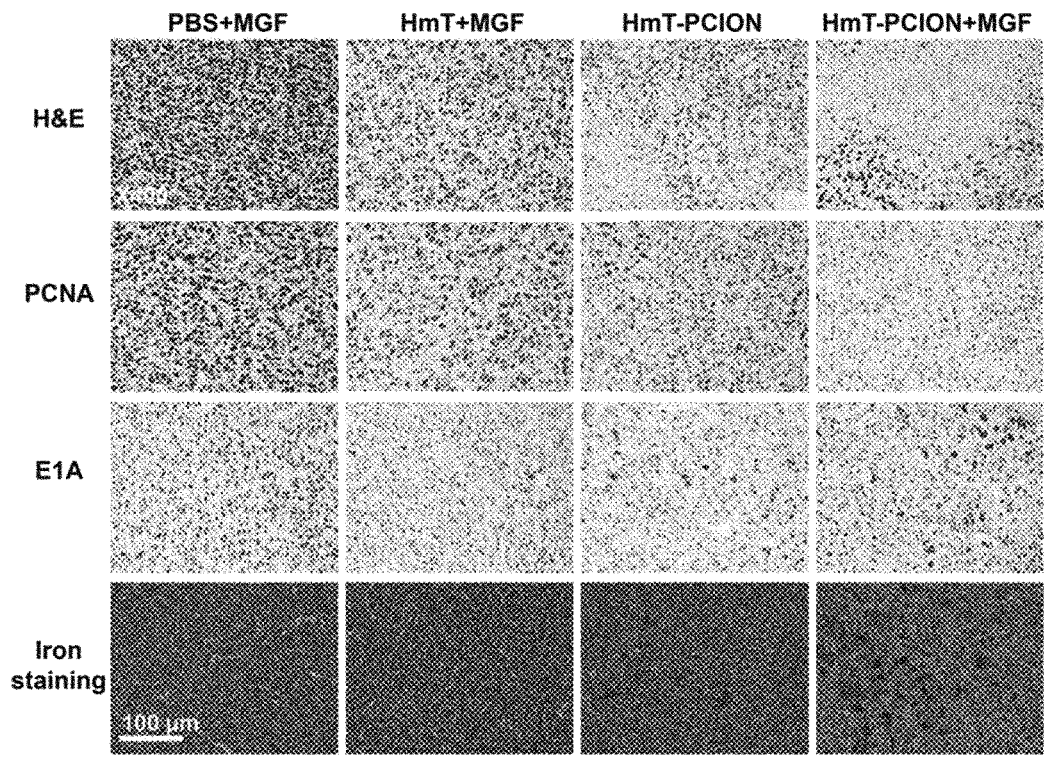
FIG. 7 illustrates microscopic images of tumor sections from each group stained with hematoxylin and eosin (H&E), immunostained against proliferating cell nuclear antigen (PCNA) or E1A, or stained against iron component, in which the images show four independent experimental results, and the original magnification is 400×.

Hematoxylin and eosin staining of tumor tissues obtained 3 days after treatment showed therapeutic changes from treatment with HmT-PCION complexes with or without an MGF. While intermediate and extended necrosis was observed in tumors treated with HmT-PCION without an MGF or HmT-PCION with an MGF, tumor tissues treated with PGS using an MGF or HmT using an MGF exhibited a large area of proliferated tumor cells (see FIG. 7). To gain greater insight into molecular mechanisms of HmT-PCION complex-mediated tumor growth inhibition, immunohistological analysis was performed. Immunostaining of tumor sections for PCNA showed fewer proliferated cancer cells in tumors injected with HmT-PCION complexes using an MGF even when compared to any other treatment methods. TO detect the degree of viral replication in tumors, tissue sections were stained with an Ad E1 A antigen-specific antibody. A very small amount of Ad E1A-positive spots were observed in naked HmT with an MGF or HmT-PCION tumors without an MGF. In clear contrast to this, numerous dark brown Ad E1A-positive spots were observed in tumors treated with HmT-PCION by application of an MGF, as consistent with the in vitro viral replication results (see FIG. 5B). This data demonstrates that PCION facilitates cancer cell uptake of HmT in the presence of an MGF and ultimately increases in situ viral replication. In addition, iron staining results are correlated with enhanced infection of antitumor Ad when it was complexed with PCION in the presence of an MGF. In summary, the staining data supports the idea that the enhanced therapeutic efficacy of HmT-PCION is attributed to the increased infection efficiency and activated replication of magnetically guided HmT-PCIONs.

The characteristics and advantages of the present disclosure are as follows:

When a complex of the present disclosure is used in magnetofection, a virus may be delivered more rapidly and efficiently into cells than in intracellular uptake of a virus by CAR-mediated endocytosis.

The present disclosure provides a pharmaceutical composition for anticancer therapy, including an antitumor virus.

When the composition of the present disclosure is used, Ad may be transduced into cells without inhibition of an intrinsic viral replication rate of antitumor Ads and antitumor effects.

Although exemplary embodiments of the present disclosure have been described in detail, it is obvious to one of ordinary skill in the art that the detailed description is provided only for illustrative purposes and is not intended to limit the scope of the present disclosure. Thus, the substantial scope of the present disclosure should be defined by the appended claims and equivalents thereof.

What is claimed is:

1. A method of treating cancer, the method comprising: administering a complex comprising: (a) magnetic nanoparticles cross-linked with catechol grafted poly-L-lysine and having PEGylated surfaces; and (b) an oncolytic andenovirus to an individual in a presence of a magnetic field, wherein a molar ratio of the magnetic nanoparticles to the oncolytic andenovirus in the complex ranges from about $1:1\times10^6$ to about $1:8\times10^7$.

2. The method of claim 1, wherein the magnetic nanoparticles comprise one selected from the group consisting of maghemite ($Fe_2O_3$), magnetite ($Fe_3O_4$), and mixtures thereof.

3. The method of claim 1, wherein in the catechol grafted poly-L-lysine, a degree of substitution of a catechol functional group with respect to the poly-L-lysine ranges from about 5 to about 30.

4. The method of claim 1, wherein the magnetic nanoparticles and the catechol grafted poly-L-lysine are mixed in a weight ratio of about 10:1 to about 1:5.

5. The method of claim 1, wherein the complex exhibits decreased liver tropism by application of an external MGF.

6. The method of claim 1, wherein the cancer is selected from the group consisting of stomach cancer, lung cancer, breast cancer, ovarian cancer, liver cancer, bronchial cancer, nasopharyngeal cancer, laryngeal cancer, pancreatic cancer, bladder cancer, colon cancer, and cervical cancer.

7. The method of claim 1, wherein the cancer comprises a coxsackievirus and adenovirus receptor (CAR) negative tumor.

* * * * *